United States Patent
Thompson

(10) Patent No.: US 9,433,597 B2
(45) Date of Patent: Sep. 6, 2016

(54) POWDERED DRINK MIX FOR RECOVERY

(71) Applicant: R. Charles Thompson, Morgan, UT (US)

(72) Inventor: R. Charles Thompson, Morgan, UT (US)

( * ) Notice: Subject to any disclaimer, the term of this patent is extended or adjusted under 35 U.S.C. 154(b) by 76 days.

(21) Appl. No.: 14/444,780

(22) Filed: Jul. 28, 2014

(65) Prior Publication Data

US 2015/0030698 A1   Jan. 29, 2015

Related U.S. Application Data

(60) Provisional application No. 61/859,398, filed on Jul. 29, 2013.

(51) Int. Cl.
| | | |
|---|---|---|
| *A61K 31/198* | (2006.01) | |
| *A61K 31/197* | (2006.01) | |
| *A23L 2/52* | (2006.01) | |
| *A23L 1/305* | (2006.01) | |
| *A23L 1/304* | (2006.01) | |
| *A23L 2/39* | (2006.01) | |

(52) U.S. Cl.
CPC .............. *A61K 31/198* (2013.01); *A23L 1/304* (2013.01); *A23L 1/3051* (2013.01); *A23L 2/39* (2013.01); *A23L 2/52* (2013.01); *A61K 31/197* (2013.01)

(58) Field of Classification Search
None
See application file for complete search history.

(56) References Cited

U.S. PATENT DOCUMENTS

| | | |
|---|---|---|
| 8,298,589 B1 | 10/2012 | Bryan |
| 8,435,570 B1 | 5/2013 | Bryan |
| 2002/0068365 A1 | 6/2002 | Kuhrts |
| 2006/0292134 A1* | 12/2006 | Stohs ................. A61K 31/19 424/94.1 |
| 2008/0233186 A1 | 9/2008 | Romero et al. |
| 2011/0104311 A1* | 5/2011 | Dooley ................ A23L 1/3002 424/725 |
| 2011/0104373 A1 | 5/2011 | Dooley et al. |

FOREIGN PATENT DOCUMENTS

| | | |
|---|---|---|
| CN | 102652743 | 3/2011 |
| WO | WO 0000212 | 1/2000 |
| WO | WO 2006102337 A2 * | 9/2006 .......... A61K 31/198 |

OTHER PUBLICATIONS

Nutilis: "Nutilis Powder", Jan. 9, 2012, Retrieved from the Internet: URL: http://nutilis.com/product/nutilis-powder, whole document.*
Nutilis Powder 2012.*

* cited by examiner

*Primary Examiner* — Robert A Wax
*Assistant Examiner* — Quanglong Truong
(74) *Attorney, Agent, or Firm* — Pate Baird, PLLC

(57) ABSTRACT

An oral product that includes an amino acid nitric oxide precursor and a compound capable of providing zinc ions. The product can be formulated as a powder and mixed with a liquid in preparation for consumption by a person. The powdered formulation may be mixed with water followed by a brief but necessary allotment of time for the powdered formulation to completely react in the water. The resulting beverage may then be consumed by a person or user to facilitate production of nitric oxide and creatine-phosphate that is usable by the person, especially to help recover and rejuvenate the person after physical exertion and reduce or relieve muscle soreness.

20 Claims, 1 Drawing Sheet

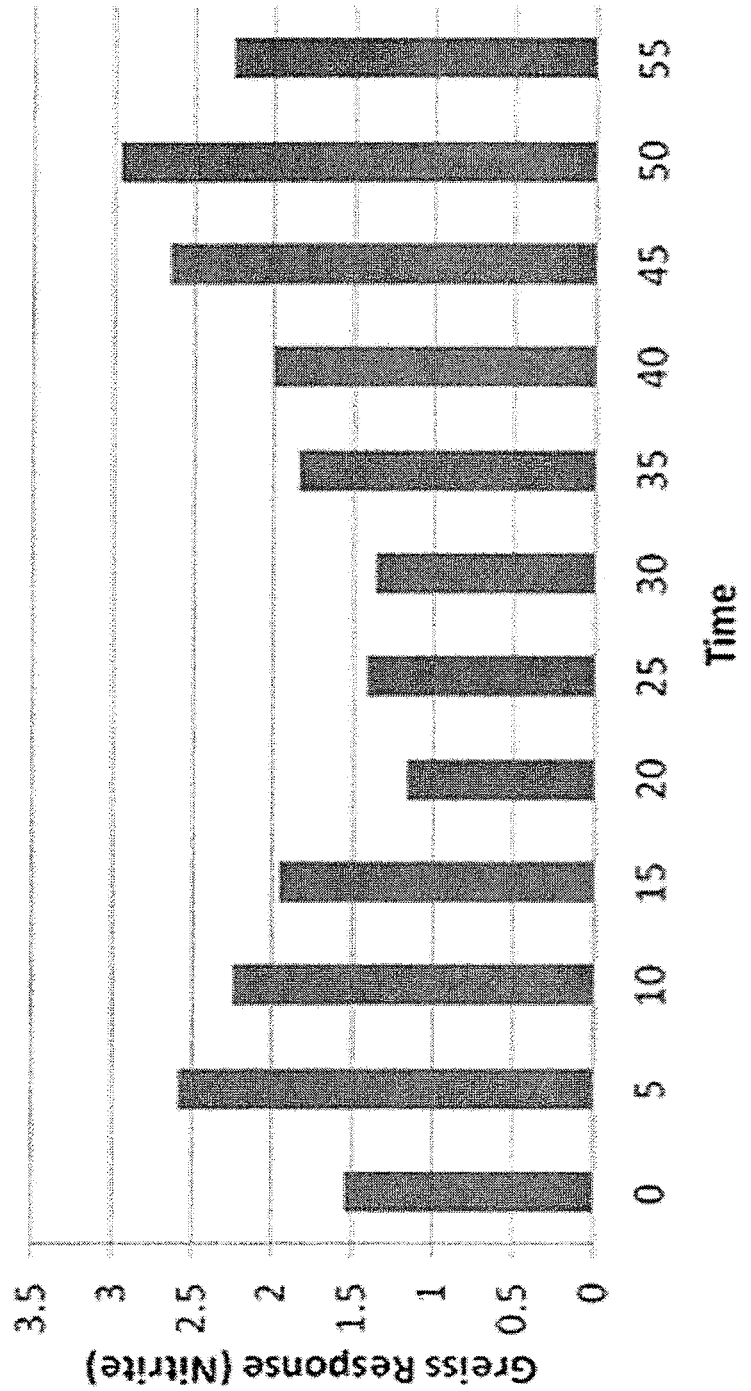

POWDERED DRINK MIX FOR RECOVERY

RELATED APPLICATIONS

This application claims the benefit of U.S. Provisional Patent Application Ser. No. 61/859,398, filed on Jul. 29, 2013, which is hereby incorporated by reference in its entirety.

BACKGROUND

1. The Field of the Invention

This invention relates to oral supplements for recovery from physical activity, and more particularly, to powdered drink mixes facilitating recovery and replenishment to the body after strenuous physical exercise or performance.

2. Background

Numerous products are currently available for helping a person recover from physical activity. These products may include attempts to replenish solutions and nutrients lost or used during exercise. These products can include a wide variety and combination of compounds to help achieve the desired effects. These products can come in a wide variety of forms, including without limitation, beverages, gels, powders, etc.

Certain products have attempted to apply the known benefits of nitric oxide and creatine-phosphate to recovery after physical exercise. Substantial literature is available on the subject of nitric oxide and its effects on human tissues.

Nitric oxide and creatine-phosphate are considered unstable molecules. This makes it difficult to develop a product that can consistently promote the formation of, or provide usable, nitric oxide and creatine-phosphate to a person. What is needed is product that provides a comparatively efficient way to promote production of nitric oxide and creatine-phosphate usable by human cells and tissues.

BRIEF SUMMARY OF THE INVENTION

In accordance with the foregoing, certain embodiments of a product, compound and method in accordance with the invention provide an oral product that can be consumed by a person to facilitate and promote the production of nitric oxide and creatine-phosphate, especially after physical exertion. The oral product may be suitably formulated to promote production of nitric oxide and creatine-phosphate in human cells and tissues.

In one embodiment, the oral product may be formulated to be a powder that is mixed with a liquid in preparation for consumption. The powdered formulation may be mixed with water, followed by a brief but necessary allotment of time for the powdered formulation to completely react in the water. The liquid may also be milk, juice, or some other suitable beverage. The resulting mixed beverage may then be consumed by a person or user to facilitate production of nitric oxide and creatine-phosphate that is usable by the person, especially to help recover and rejuvenate the person after physical exertion and reduce or relieve muscle soreness.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through the use of the accompanying drawings in which:

FIG. 1 is a graph showing example results demonstrating the presence of nitrite in a person's saliva via the Greiss test.

DETAILED DESCRIPTION OF THE PREFERRED EMBODIMENTS

It will be readily understood that the components of the present invention, as generally described herein, could be arranged and designed in a wide variety of different configurations or formulations. Thus, the following more detailed description of the embodiments of the system, product and method of the present invention, is not intended to limit the scope of the invention, as claimed, but is merely representative of various embodiments of the invention.

In one embodiment, the oral product may be formulated as a powder. The powder may be formulated to include any or all of the following: arginine, creatine, calcium carbonate, zinc carbonate, di-potassium phosphate, sodium bi-carbonate, monosaccharide, disaccharide, tri-saccharide, lipoic acid, niacin, riboflavin, folic acid, ascorbic acid, citric acid, malic acid, and sucrose.

In one embodiment, arginine can comprise approximately 31.0% of the mass of the powdered product, or may have a molar ratio with respect to creatine of approximately 1.00. Arginine has the following molecular formula: $C_6H_{14}N_4O_2$. Arginine is an amino acid and the L-form is a common, natural amino acid. Arginine is considered a precursor for the synthesis of nitric oxide. Any suitable amino acid nitric oxide precursor may be used, for example and not by way of limitation, lysine.

In one embodiment, creatine, or creatine.$H_2O$, can comprise approximately 23.4% of the mass of the powdered product, or may have a molar ratio with respect to arginine of approximately 1.00. Creatine in the form as used herein has the following molecular formula: $C_4H_9N_3O_2.H_2O$. Creatine is considered a precursor to creatine-phosphate. Any suitable creatine salt may be used, for example and not by way of limitation, creatine alphaketoglutarate and creatine pyruvate.

In one embodiment, calcium carbonate can comprise approximately 1.54% of the mass of the powdered product, or may have a molar ratio with respect to arginine of approximately 0.216. Calcium carbonate has the following molecular formula: $CaCO_3$. Calcium carbonate can be used as a calcium supplement.

In one embodiment, zinc carbonate can comprise approximately 0.181% of the mass of the powdered product, or may have a molar ratio with respect to arginine of approximately 0.0155. Zinc carbonate has the following molecular formula: $ZnCO_3$. Zinc carbonate can be used as a zinc supplement. Use of zinc ions can promote nitric oxide production in cells. The zinc dimer may be considered more active in the production of nitric oxide. Any suitable compound capable of providing the intended zinc ions may be used, for example and not by way of limitation, zinc carbonate, zinc chloride, zinc oxide, and zinc hydroxide.

In one embodiment, di-potassium phosphate can comprise approximately 1.62% of the mass of the powdered product, or may have a molar ratio with respect to arginine of approximately 0.0521. Di-potassium phosphate has the following molecular formula: $HK_2O_4P$. Di-potassium phosphate can be used as a buffering agent and a common source of potassium and phosphorous.

In one embodiment, sodium bi-carbonate can comprise approximately 0.003% of the mass of the powdered product, or may have a molar ratio with respect to arginine of approximately 0.054. Sodium bi-carbonate has the following molecular formula: $NaHCO_3$. Sodium bi-carbonate can be used in numerous ways, including neutralization of acids and bases.

In one embodiment, lipoic acid can comprise approximately 0.154% of the mass of the powdered product, or may have a molar ratio with respect to arginine of approximately 0.00419. Lipoic acid has the following molecular formula: $C_8H_{14}O_2S_2$. Lipoic acid can be used for a wide variety of health benefits and can effect nitric synthetase dispersion.

In one embodiment, niacin can comprise approximately 0.769% of the mass of the powdered product, or may have a molar ratio with respect to arginine of approximately 0.0351. Niacin has the following molecular formula: $C_6H_5NO_2$. Niacin, vitamin $B_3$, can be used as a dietary supplement.

In one embodiment, riboflavin can comprise approximately 0.077% of the mass of the powdered product, or may have a molar ratio with respect to arginine of approximately 0.00115. Riboflavin has the following molecular formula: $C_{17}H_{20}N_4O_6$. Riboflavin, vitamin $B_2$, can be used as a dietary supplement. Riboflavin-5'-phosphate ($C_{17}H_{21}N_4O_9P$) may be substituted for riboflavin in a similar, corresponding ratio.

In one embodiment, folic acid can comprise approximately 0.015% of the mass of the powdered product, or may have a molar ratio with respect to arginine of approximately 0.000196. Folic acid has the following molecular formula: $C_{19}H_{19}N_7O_6$. Folic acid, vitamin $B_9$, can be used as a dietary supplement.

In one embodiment, ascorbic acid can comprise approximately 5.77% of the mass of the powdered product, or may have a molar ratio with respect to arginine of approximately 0.184. Ascorbic acid has the following molecular formula: $C_6H_8O_6$. Ascorbic acid, vitamin C, can be used as a dietary supplement.

In one embodiment, citric acid can comprise approximately 6.54% of the mass of the powdered product, or may have a molar ratio with respect to arginine of approximately 0.191. Citric acid has the following molecular formula: $C_6H_8O_7$. Citric acid can be used as a dietary supplement and natural preservative.

In one embodiment, malic acid can comprise approximately 8.46% of the mass of the powdered product, or may have a molar ratio with respect to arginine of approximately 0.354. Malic acid has the following molecular formula: $C_4H_6O_5$. Malic acid can be used as a dietary supplement.

In one embodiment, sucrose can comprise approximately 20.5% of the mass of the powdered product. Sucrose has the following molecular formula: $C_{12}H_{22}O_{11}$. Sucrose can be used as a dietary supplement and sweetener. Other simple sugars may also be used, including without limitation, monosaccharides, other disaccharides, and tri-saccharides. Any appropriate sweetener may be substituted in an appropriate amount, for example and not by way of limitation, stevia.

The mass percentage of the components that comprise a powdered oral product may be adjusted plus or minus 20%. Other components may be added as desired, such as flavors or other preservatives or other dietary supplements.

The amount of arginine and creatine used is intended to have a molar ratio between approximately 1:1 and 5:1. Organic acids help provide maximum solubility of active substrates like arginine and creatine, which helps solubilize arginine and creatine at specific molar ratios. The amount of organic acids used is intended to provide a specific pH range, which pH range is generally considered to be lower than a pH of 6, or approximately a pH of 5, but may be anywhere between an approximate pH of 8 and an approximate pH of 2.

The amount of simple sugars used may have a molar ratio of approximately 1:5 or 5:1 in any combination with arginine, creatine, and zinc ions.

Certain components can be excluded while still allowing the powdered product to provide the intended result. For example and not by way of limitation, vitamins provided as part of the formulation may be supplied by a separate source other than the oral product.

However, the presence of zinc in the form of zinc ions is instrumental in the effectiveness of any oral product. Thus, zinc in the form of zinc ions should be included in combination with any or all of the component ingredients of the oral product.

Simple and complex carbohydrates may be included in the formulation of the oral product to help promote recovery from physical exercise.

In one embodiment, the oral product may be formulated in powdered form. The oral product may then be mixed thoroughly with a liquid, such as water. The mixture should be allowed to stand for at least one minute before consumption, and preferably between approximately one and five minutes.

As shown in FIG. 1, experimental data can show the presence of nitrite in the person's saliva after consumption of the mixture. The correlation between nitrite in saliva and nitric oxide production has been demonstrated previously in separate, peer reviewed literature.

As an example, a person combined the powdered formulation as generally described herein with water. The powdered formulation and water were stirred to form a mixed beverage. The mixed beverage was allowed to stand for approximately three minutes. The person then consumed the mixed beverage.

After approximately five (5) minutes, when monitored for nitrite via the Greiss test, the person's saliva can be shown to have produced a measured increase and clearing of nitric oxide over a 90 minute time period. This positive test demonstrates that nitric oxide had been produced, and was present in the person's system.

What is claimed and desired to be secured by United States Letters Patent is:

1. An oral dietary supplement for producing nitric oxide and creatine phosphate in a user comprising:
   an amino acid nitric oxide precursor selected from the group consisting of arginine and lysine;
   a creatine salt selected from the group consisting of creatine alphaketoglutarate, creatine pyruvate, and creatine.$H_2O$;
   a simple sugar; and
   a compound capable of providing zinc ions selected from the group consisting of zinc carbonate, zinc chloride, zinc oxide, and zinc hydroxide.

2. The oral dietary supplement of claim 1, further comprising at least one B vitamin.

3. The oral dietary supplement of claim 1, wherein the molar ratio of amino acid to creatine salt to simple sugar is approximately 2:1:2.

4. The oral dietary supplement of claim 3, further comprising at least three organic acids and having a pH of approximately 5.

5. The oral dietary supplement of claim 1, wherein the molar ratio of amino acid to creatine salt to simple sugar to compound capable of providing zinc ions is approximately 1:1:2:3.

6. The oral dietary supplement of claim 3, wherein the supplement is in a powdered formulation.

7. A method for using an oral dietary supplement for producing nitric oxide in a user comprising:
   providing a powder that comprises an amino acid nitric oxide precursor, a creatine salt, a simple sugar, and a compound capable of providing zinc ions;
   mixing the powder with a liquid to form a mixed beverage;
   allowing the mixed beverage to stand for approximately three (3) minutes before consuming;
   consuming the mixed beverage by a user; and
   producing nitric oxide in the user.

8. The method of claim 7, wherein the powder has a molar ratio of amino acid to creatine salt to simple sugar of approximately 2:1:2.

9. The method of claim 7, wherein the powder has a molar ratio of amino acid to creatine salt to simple sugar to compound capable of providing zinc ions of approximately 2:1:2:3.

10. The method of claim 8, wherein the powder further comprises at least one B vitamin.

11. The method of claim 8, wherein the powder further comprises at least two organic acids and has a pH of approximately 5.

12. The method of claim 8, wherein the liquid is milk.

13. The method of claim 7, wherein the mixed beverage is allowed to stand from approximately at least one (1) minute to approximately five (5) minutes.

14. A method for using an oral dietary supplement for producing nitric oxide and creatine phosphate in a user comprising:
   providing a powder that comprises an amino acid selected from the group consisting of arginine and lysine, a creatine salt selected from the group consisting of creatine alphaketoglutarate, creatine pyruvate, and creatine.$H_2O$, a simple sugar, and a compound capable of providing zinc ions selected from the group consisting of zinc carbonate, zinc chloride, zinc oxide, and zinc hydroxide;
   mixing the powder with a liquid to form a mixed beverage;
   allowing the mixed beverage to stand for approximately three (3) minutes before consuming;
   consuming the mixed beverage by a user; and
   producing nitric oxide and creatine phosphate in the user.

15. The method of claim 14 wherein the molar ratio of the amino acid to the creatine salt to the simple sugar is approximately 2:1:2.

16. The method of claim 14 wherein the molar ratio of the amino acid to the creatine salt to the simple sugar to the compound capable of providing zinc ions is approximately 1:1:2:2.

17. The method of claim 16 wherein the powder further comprises at least three (3) vitamins.

18. The method of claim 17 wherein the powder further comprises sodium bi-carbonate and di-potassium phosphate.

19. The method of claim 18 wherein the mixed beverage is allowed to stand for at least five (5) minutes.

20. The method of claim 15 wherein the powder further comprises at least two organic acids and has a pH of less than 6.

\* \* \* \* \*